United States Patent
Blanckenfiell et al.

(10) Patent No.: US 9,327,240 B2
(45) Date of Patent: May 3, 2016

(54) METHOD AND SYSTEM FOR ESTIMATING REAGENT QUALITY

(75) Inventors: Magnus Blanckenfiell, Hisings Kärra (SE); Per-Olof Källen, Västra Frölunda (SE)

(73) Assignee: Volvo Truck Corporation, Göteborg (SE)

(*) Notice: Subject to any disclaimer, the term of this patent is extended or adjusted under 35 U.S.C. 154(b) by 0 days.

(21) Appl. No.: 14/417,798

(22) PCT Filed: Aug. 31, 2012

(86) PCT No.: PCT/EP2012/003658
§ 371 (c)(1),
(2), (4) Date: Jan. 28, 2015

(87) PCT Pub. No.: WO2014/032686
PCT Pub. Date: Mar. 6, 2014

(65) Prior Publication Data
US 2015/0209730 A1      Jul. 30, 2015

(51) Int. Cl.
*G01N 15/06*       (2006.01)
*G01N 33/00*       (2006.01)
(Continued)

(52) U.S. Cl.
CPC ........ *B01D 53/9495* (2013.01); *B01D 53/9431* (2013.01); *F01N 3/208* (2013.01); *F01N 11/00* (2013.01); *G01N 33/0037* (2013.01); *F01N 2550/05* (2013.01); *F01N 2560/026* (2013.01); *F01N 2610/02* (2013.01);
(Continued)

(58) Field of Classification Search
CPC ....... G01N 15/06; G01N 33/00; G01N 33/48; F01N 3/2013; F01N 3/20; F01N 3/00; F01N 3/18; F01N 3/208; F01N 3/2066; F01N 11/00; F01N 2550/02

USPC ............. 436/43, 108, 116, 117, 118; 60/287, 60/274, 277, 299, 286, 297, 301, 303
See application file for complete search history.

(56) References Cited

U.S. PATENT DOCUMENTS

| | | | |
|---|---|---|---|
| 7,241,431 B2 * | 7/2007 | Fischer | 423/239.1 |
| 7,426,825 B2 * | 9/2008 | Viola et al. | 60/286 |
| 2004/0074229 A1 * | 4/2004 | Upadhyay et al. | 60/286 |
| 2008/0178575 A1 | 7/2008 | Shaikh et al. | |
| 2010/0205940 A1 | 8/2010 | Toshioka et al. | |

(Continued)

FOREIGN PATENT DOCUMENTS

DE    102010000626 A1    9/2010

OTHER PUBLICATIONS

International Search Report (May 23, 2013) for corresponding International App. PCT/EP2012/003658.

(Continued)

*Primary Examiner* — Brian J Sines
(74) *Attorney, Agent, or Firm* — WRB-IP LLP

(57) ABSTRACT

In a method for estimating the quality of an urea based reagent in terms of urea concentration, the reagent is injected upstream of a SCR catalyst in an exhaust aftertreatment system. A demanded NOx conversion rate is set substantially lower than a currently estimated maximum NOx conversion rate of the SCR catalyst. An actual NOx conversion rate is monitored for a certain time period. The urea concentration of the reagent is estimated based on comparing the monitored actual NOx conversion and the demanded NOx conversion during the time period. A corresponding system is also disclosed.

15 Claims, 2 Drawing Sheets

(51) Int. Cl.
   *G01N 33/48*   (2006.01)
   *F01N 3/20*    (2006.01)
   *F01N 3/00*    (2006.01)
   *B01D 53/94*   (2006.01)
   *F01N 11/00*   (2006.01)

(52) U.S. Cl.
   CPC .......... *F01N 2900/0418* (2013.01); *F01N 2900/1621* (2013.01); *F01N 2900/1814* (2013.01); *Y02T 10/24* (2013.01); *Y02T 10/47* (2013.01); *Y10T 436/171538* (2015.01)

(56) References Cited

U.S. PATENT DOCUMENTS

2012/0000270 A1    1/2012  Narita
2012/0260634 A1*  10/2012  Devarakonda et al. ......... 60/274

OTHER PUBLICATIONS

International Preliminary Report on Patentability (Nov. 11, 2014) for corresponding International App. PCT/EP2012/003658.

* cited by examiner

METHOD AND SYSTEM FOR ESTIMATING REAGENT QUALITY

BACKGROUND AND SUMMARY

This invention relates to a method for estimating the quality of a urea based reagent, and an exhaust aftertreatment system that is arranged to estimate the quality of a urea based reagent. The method is particularly applicable on diesel combustion engines, for example installed in a medium or heavy truck, a bus, constructional vehicles, or the like.

The invention relates, according to an aspect thereof, to exhaust aftertreatment systems comprising Selective Catalytic Reduction (SCR) catalysts, in which NOx continuously is removed through active injection of a reagent into the exhaust gas mixture entering the catalyst. This type of NOx reduction system is known for achieving a high NOx conversion efficiency. Urea based SCR catalysts use gaseous ammonia as the active NOx reducing regent. Typically, an aqueous solution of urea is carried on board of a vehicle, and an injection system is used to supply it into the exhaust gas stream entering the SCR catalyst where it decomposes into hydro cyanic acid (NHCO) and gaseous ammonia (NH3), which then reacts with the SCR catalyst, converting NOx in the exhaust stream into harmless nitrogen and water.

Different emission legislations require monitoring of the reagent quality to prevent drivers from diluting the urea with water or other fluids. A diluted aqueous solution of urea will directly affect vehicle output NOx emission levels.

It is known to simply use a reagent quality sensor, for example for detecting the quality of the urea. One known sensor technique involves the use of ultrasonic density measurements or electrical characterisation of the reagent. The reagent density as such is however no definitive indication of diluted reagent because many fluids have similar density as the standard aqueous solution of urea, such as for example washer fluid, coolant, salt water. Dilution of the reagent could thus occur undetected. Furthermore, urea quality sensors are expensive and results in increased maintenance costs.

Another solution for detection dilution of the aqueous solution of urea is shown in document DE 10 2010 000 626 A1, where the NOx conversion rate after an engine stop is compared with the NOx conversion rate just before the engine stop. If the NOx conversion rate differs before and after the engine stop, it is concluded that the aqueous solution of urea has been diluted during the stop. A problem with this urea quality diagnosing method is that dilution occurring with the engine running is not detected. Furthermore, other changes affecting the NOx conversion rate made during standstill of the vehicle may result in the erroneous conclusion of reagent dilution.

There is thus a need for an improved method for monitoring reagent quality, which removes the above mentioned disadvantages.

It is desirable to provide a method for estimating the quality of an urea based reagent in terms of urea concentration, wherein said reagent being injected upstream of a SCR catalyst in an exhaust aftertreatment system, where the previously mentioned problem is at least partly avoided.

According to an aspect of the present invention, a method includes
setting a demanded NOx conversion rate substantially lower than a currently estimated maximum NOx conversion rate of said SCR catalyst;
monitoring an actual NOx conversion rate for a certain time period; and estimating the urea concentration of said reagent based on comparing the monitored actual NOx conversion and the demanded NOx conversion during said time period.

It is also desirable to provide an exhaust aftertreatment system for a combustion engine comprising at least a SCR catalyst, a reagent injector arranged upstream of said SCR catalyst, a NOx sensor arranged downstream of said SCR catalyst, and an electronic control unit for controlling dosage of said reagent, where the previously mentioned problem is at least partly avoided.

According to an aspect of the invention, an exhaust aftertreatment system is provided, wherein said electronic controller being arranged to estimate the quality of a urea based reagent in terms of urea concentration by:
setting demanded NOx conversion rate substantially lower than a currently estimated maximum NOx conversion rate of said SCR catalyst; monitoring an actual NOx conversion rate for a certain time period; and calculating an estimate of the urea concentration of said reagent based on comparing the monitored actual NOx conversion and the demanded NOx conversion during said time period.

The inventive method and system aims, according to aspects thereof, to estimate the reagent quality based merely on determined NOx conversion efficiency of the SCR catalyst. This has the advantage of eliminating the need of a costly additional urea quality sensor, and the total exhaust aftertreatment system can be made less complex. It is however difficult to determine the root cause of poor SCR catalyst NOx conversion. Possible reasons behind a poor NOx conversion, other than a diluted reagent, may for example be a degraded and aged SCR catalyst. A degraded SCR catalyst has a reduced NH3 storage capacity and reduced maximum NOx conversion rate. The inventive method and system relies on the fact that a degraded SCR catalyst is still capable of providing a demanded NOx conversion rate, but a reduced NOx conversion rate. The degradation of a SCR catalyst is thus mainly noticeable at higher demanded NOx conversion rates. A degraded and aged SCR catalyst exhibits essentially the same NOx conversion rate as a new SCR catalyst at relatively low demanded NOx conversion rate. This SCR catalyst characteristic is used by the method and system according to the invention, in that the reagent quality monitoring is performed at a reduced level of demanded NOx conversion rate compared with a currently estimated maximum NOx conversion rate of said SCR catalyst. Thereby, any degradation and aging effects of the SCR catalyst may be more or less eliminated, and the result from comparing demanded and actual NOx conversion rates corresponds more or less directly to the quality of the reagent injected during the test period.

The method may additionally include the step of ensuring that any stored ammonia within said SCR catalyst does not influence the outcome of said urea concentration estimation. If the SCR catalyst ammonia buffer is changed during the test period, for example increased, and this increase is not taken into account when estimating the urea concentration of the reagent, an unknown amount of ammonia originating from the reagent has become adsorbed on the catalyst substrate and stored in the SCR catalyst during the test. However, the urea concentration estimate of the reagent according to the invention is based on comparing the accumulated amount of injected reagent with the accumulated NOx reduction amount in the SCR catalyst during the test period. The accumulated NOx reduction amount in the SCR catalyst during the test period may for example be measured by means of a NOx sensor installed downstream the SCR catalyst and an additional NOx sensor installed upstream of the reagent injector, and simply integrating the difference in a sensor output during the test period, or by replacing the additional NOx sensor with an estimate of the NOx level in the exhaust gas upstream the SCR catalyst. The urea concentration estimate of the reagent is further based on a model for describing the actual conversion of NOx inside the SCR catalyst. This model may for example be based on a mass or volumetric flow rate of the exhaust gas during the test period, a NO/NO2 ratio of the exhaust gas entering the SCR catalyst, and a predictive NH3-NO/NO2 reaction model for the SCR catalyst, and a SCR catalyst exhaust gas temperature.

The step of ensuring that any stored ammonia within said SCR catalyst does not influence the outcome of said urea concentration estimation may in the simplest approach be realised by controlling a reagent injection rate before and during said time period such that said SCR catalyst ammonia buffer remains substantially empty during said time period. An estimate of the ammonia buffer of the SCR catalyst is often more or less continuously updated based on engine settings and load, reagent injection rates, exhaust gas NOx levels before and after the SCR catalyst, etc. It is thus possible to use said ammonia buffer estimate, the engine settings, and the reagent injection rate to ensure that the SCR catalyst ammonia buffer remains substantially empty during said time period.

The step of ensuring that any stored ammonia within said SCR catalyst does not influence the outcome of said urea concentration estimation may alternatively be realised by controlling a reagent injection rate during said time period such that an estimated SCR catalyst ammonia storage level at the start and end of said time period is the same. This will also ensure that all injected urea is included in the urea concentration estimate of the reagent.

The method may additionally include the step of setting said demanded NOx conversion rate such that ammonia slip out of said SCR catalyst is prevented. Ammonia slip out of the SCR catalyst may occur if all ammonia entering the SCR catalyst is not adsorbed by the catalyst, and consequently passes the catalyst unreacted. Ammonia slip contributes to the total nitrogen emission from the vehicle and is regulated to a maximum value by legislation in some countries. Furthermore, since the reagent quality estimation is based on comparing the accumulated reagent injection amount and the accumulated SCR catalyst NOx conversion during the test period, any ammonia slip will distort the reagent quality estimation because it is assumed that all ammonia originating from the injected reagent has been converted in the catalyst. Moreover, most NOx sensors are cross-sensitive to NOx and ammonia, such that ammonia slip may be considered as NOx emission, thereby distorting the actual registered SCR catalyst NOx conversion rate, and consequently also distorting the resulting urea concentration estimation. Ammonia slip out of said SCR catalyst is prevented by simply setting said demanded NOx conversion rate sufficiently low, which here implies setting the reagent injection rate sufficiently low. At a sufficiently low reagent injection rate, taking into account current engine NOx emission levels and the SCR catalyst ammonia buffer level, all ammonia entering the catalyst will adsorb on the catalyst substrate, and subsequently catalytically react with NOx and become converted into nitrogen molecules (N2) and water, such that no unreacted ammonia will pass through the catalyst unreacted.

The method may additionally include the step of setting said demanded NOx conversion rate at least 10% lower than a currently estimated maximum NOx conversion rate of said SCR catalyst, specifically at least 20% lower, and more specifically at least 30% lower. As described above, the reduction in demanded NOx conversion rate serves to improve the accuracy of the urea quality estimation. Firstly, it reduces the influence of a degraded and aged SCR catalyst, secondly, it avoids building up, or at least not increasing, the SCR catalyst ammonia buffer, and thirdly, it reduces the likelihood of ammonia slip.

The currently estimated maximum NOx conversion rate of said SCR catalyst may be continuously monitored during the life time of the SCR catalyst for the purpose of minimising the level of reduced demanded NOx conversion rate during the test period with a less significant amount. The current maximum NOx conversion rate of the SCR catalyst may for example be estimated by slowly increasing the reagent injection rate until a ammonia slip is detected, which event indicates the current maximum NOx conversion rate, possibly taking into account the effects of an ammonia slip catalyst. The current maximum NOx conversion rate of the SCR catalyst may alternatively, or in addition to the above described test, be estimated by a SCR catalyst degradation software model that may be based on various input parameters, such as accumulated NOx conversion, engine settings, fuel quality, reagent dosing strategy, etc.

The currently estimated maximum NOx conversion rate of the SCR catalyst may alternatively simply be considered corresponding to the maximum NOx conversion rate of a new SCR catalyst. This would however often require a more significantly reduced demanded NOx conversion rate during the test period for compensating a potentially degraded SCR catalyst. Typically, this approach may lead to setting of said demanded NOx conversion rate in a range of 10-50% of a currently estimated maximum NOx conversion rate of said SCR catalyst, specifically in a range of 10-40%, and more specifically in a range of 10-30%.

The method may additionally include the step of selecting said time period according to a predetermined value, or determining said time period based on actual engine and/or exhaust aftertreatment system parameters. A fixed predetermined time period will often result in a less accurate estimation because a low current low exhaust gas flow would then lead to a low accumulated level of actual NOx conversion. Selection of the time period according to actual engine and/or exhaust aftertreatment system parameters will often for the same reasons lead to a more accurate urea quality estimation, and preferably is the time period based on accumulated level of engine NOx emission during said time period.

The estimation of said urea concentration of said reagent may be based on calculating a ratio between said actual NOx conversion and said demanded NOx conversion, and multiplying said ratio with a factor corresponding to an expected proportion of urea in said reagent. The factor may for example be 32.5 when the reagent is Adblue™.

The actual NOx conversion during said time period is preferably calculated by integrating the difference between a NOx emission level upstream of said SCR catalyst and a NOx emission level downstream of said SCR catalyst during said time period. The NOx emission level upstream of said SCR catalyst is either measured by a NOx sensor, or calculated based on engine settings, engine load, engine speed, etc. The NOx emission level downstream of said SCR catalyst is mostly measured by as NOx sensor.

The demanded NOx conversion during said time period is calculated by integrating the product of said demanded NOx conversion rate and a measured or estimated NOx emission level upstream of said SCR catalyst during said time period.

The reagent quality estimation test may be triggered in several ways. For example, the reagent quality estimation may be triggered upon determining on at least two occasions within a certain time period that the SCR catalyst ammonia buffer is empty, wherein a time interval of elevated reagent dosage rate has occurred between said at least two occasions on order to restore said SCR catalyst ammonia buffer. Many other triggering mechanisms are possible and within the scope of the invention.

The step of setting a demanded NOx conversion rate may comprise the step of controlling the amount of injected reagent upstream of the SCR catalyst in the exhaust aftertreatment system based on actual engine and/or exhaust aftertreatment system parameters.

BRIEF DESCRIPTION OF DRAWINGS

In the detailed description of the invention given below reference is made to the following figure, in which.

DETAILED DESCRIPTION

Various aspects of the invention will hereinafter be described in conjunction with the appended drawings to illustrate and not to limit the invention, wherein like designations denote like elements, and variations of the inventive aspects are not restricted to the specifically shown embodiment, but are applicable on other variations of the invention.

Figure 1:
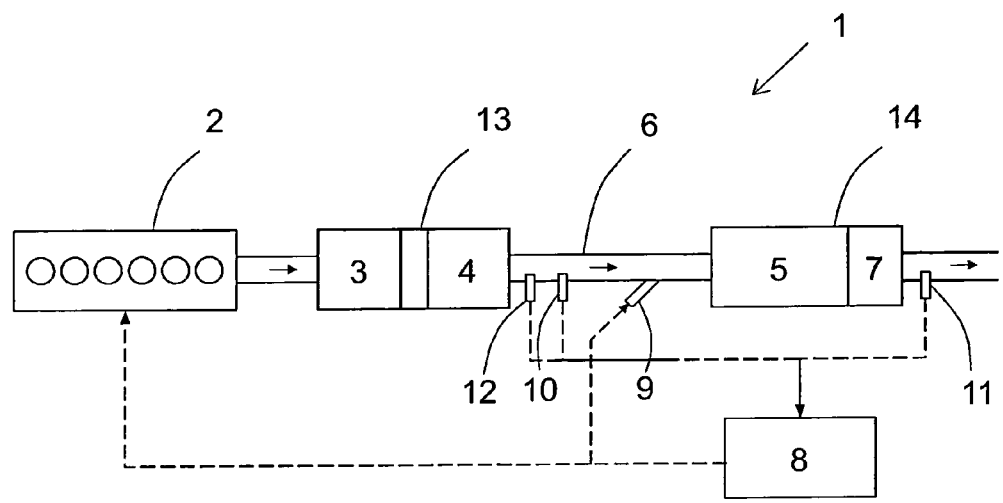
FIG. 1 shows a layout of an exhaust aftertreatmnent system.

FIG. 1 shows schematically an exemplary layout of an exhaust aftertreatment system 1 of a diesel engine 2, in particular for a heavy truck or bus, or the like. The specific exhaust aftertreatment system 1 shown includes a unit 13 comprising a diesel oxidation catalyst 3 and a particulate filter 4 to reduce the level of carbon monoxide (CO), hydrocarbons (HC), and particulate matter. NOx emission from the engine 2 must also be reduced to comply with regulatory emission standards, and a SCR catalyst 5 is installed along the exhaust gas pipe 6 for this reason. Selective catalytic reduction is a means of converting NOx with the aid of a catalyst into nitrogen ($N_2$) and water ($H_2O$). A reagent, typically urea mixed with water, is added to the exhaust gas stream upstream of the SCR catalyst 5 by means of a reagent injector 9, and converted to ammonia upon hydrolysis, which ammonia is adsorbed onto the SCR catalyst 5. The SCR catalyst 5 may be of the iron- or copper-based zeolite type, or vanadium-based type. An ammonia slip catalyst 7 may be installed downstream of the SCR catalyst 5, and forms jointly with the SCR catalyst 5 a single unit 14. An ammonia slip catalyst often functions by converting unreacted ammonia ($NH_3$) out of the SCR catalyst to $N_2$ and $H_2O$ by means an ammonia oxidation catalyst. An electronic control unit 8 associated with the exhaust aftertreatment system 1 may be configured to control reagent injection at the reagent injector 9 upstream of the SCR catalyst 5 by means of a reagent dosing model, which may use different parameters as input signals, such as temperature of the exhaust gas entering the SCR catalyst 5 as provided by a temperature sensor 10. Alternatively, a temperature sensor may be provided on each side of the SCR catalyst, and a mean value of these two sensors may by supplied to the electronic control unit 8. A NOx sensor 11 located downstream of the SCR catalyst 5 is provided to primarily detect the level of NOx emission in the exhaust gas. However, the NOx sensor 11 is cross-sensitive also to ammonia. An additional NOx sensor 12 is preferably installed upstream of the SCR catalyst 5, such that SCR conversion efficiency can be accurately determined. Note here that the invention is equally applicable on a less complex exhaust aftertreatment system, which for example only comprises the SCR catalyst 5, the reagent injector 9, and the NOx sensor 11 for measuring current NOx emission level out of the SCR catalyst.

Figure 2:
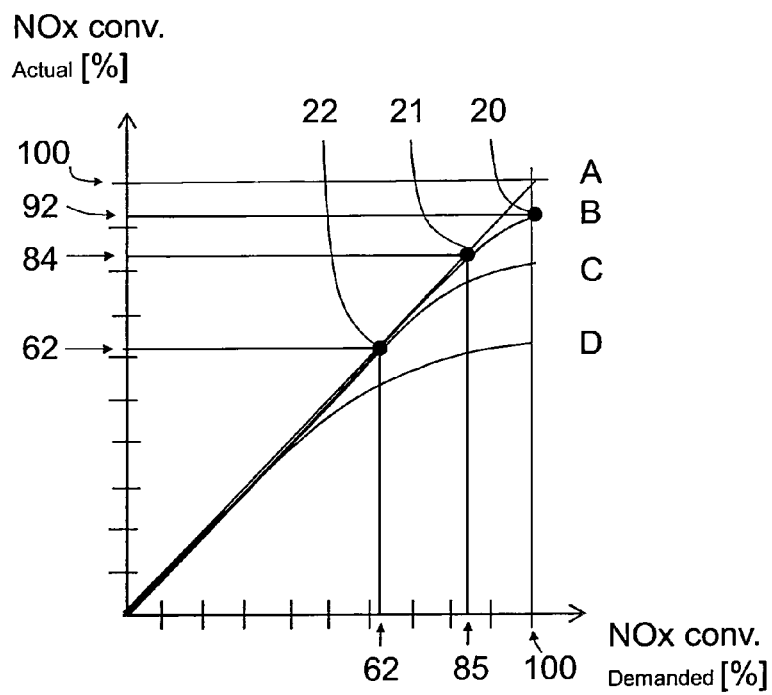
FIG. 2 shows the degradation effects of a SCR catalyst.

A key aspect of the invention is, as far as possible, to achieve a direct relation between the SCR catalyst NOx conversion efficiency and the reagent quality, i.e. to eliminate any negative influence of a degraded, aged and/or poisoned SCR catalyst 5. This is achieved by using the fact that a degraded SCR catalyst 5 still is able to meet a demanded NOx conversion rate, if said demanded NOx conversion rate reduced with respect to a maximum SCR catalyst 5 NOx conversion rate that is currently achievable. This SCR catalyst characteristic is schematically illustrated in FIG. 2, which shows an X-Y diagram with demanded NOx conversion rate in percent [%] on the X-axis, and actual NOx conversion rate in percent [%] on the Y-axis, and exemplary SCR catalyst characteristics plotted for four different SCR catalyst degradation levels. The curves A-D here correspond to exemplary SCR catalyst characteristics, where A depicts the function of a new SCR catalyst, curve B a slightly degraded SCR catalyst, curve C a more degraded SCR catalyst, and curve D an even more degraded SCR catalyst.

The SCR characteristic corresponding to curve A is more or less a linear function due to the exceptionally good NOx conversion rate that is achievable by a state of the art SCR catalyst. At 100% demanded NOx conversion, an actual NOx conversion rate of more than 95% is generally achievable, and under optimal conditions even above 97%. In FIG. 2, 100% actual NOx conversion has been illustrated for sake of simplicity.

SCR characteristic B corresponds to characteristic A to a large degree, and differs mainly at upper levels demanded NOx conversion rates. Due to a slight degradation, the SCR catalyst of the B characteristic has a slight reduced ammonia adsorption capacity, both in terms of ammonia storage level and ammonia adsorption rate. As a consequence, at 100% demanded NOx conversion, only about 92% NOx conversion rate is attained. Moreover, due to the degraded capacity of the SCR catalyst, a certain level of ammonia slip will likely occur at 100% demanded NOx conversion, which ammonia slip may be completely or at least partly converted in a following ammonia slip catalyst 7.

To avoid excessive ammonia slip, a currently estimated maximum achievable actual NOx conversion rate of the SCR catalyst may be monitored and taken into account when setting demanded NOx conversion rate. For example, as illustrated in FIG. 2 with respect to curve B, the currently estimated maximum achievable actual NOx conversion rate of the SCR catalyst is here estimated to about 92% for 100% demanded NOx conversion rate (point 20). Since this operating point 20 may result in excessive ammonia slip due to the degraded catalyst, demanded NOx conversion operating point may be reduced to about 85% (point 21), which result in about 84% actual NOx conversion ratio and reduced level of ammonia slip.

The method for estimating the quality according to the invention comprises a time period when the actual NOx conversion rate is monitored, and at least during this time period should the demanded NOx conversion rate be reduced to eliminate, as far as possible, the effect of a degraded SCR catalyst. In FIG. 2, this corresponds to having an operation point along the diagonal, i.e. along curve A, because the estimation of the urea concentration of the reagent is based on calculating a ratio between an actual NOx conversion and a demanded NOx conversion, and multiplying the ratio with a factor corresponding to an expected proportion of urea in the reagent. Hence, if the ratio between the actual NOx conversion and a demanded NOx conversion differs from unity (1.0) due to catalyst degradation reasons, the resulting urea quality estimation will be distorted. The actual NOx conversion during said time period is here calculated by integrating the difference between a NOx emission level upstream of the SCR catalyst and a NOx emission level downstream of the SCR catalyst during the time period, and the demanded NOx conversion during the time period is here calculated by integrating the product of the demanded NOx conversion rate and a NOx emission level upstream of the SCR catalyst during the time period. For example, the demanded NOx conversion rate may be set to at least 10% lower than currently estimated maximum NOx conversion rate of said SCR catalyst, specifically at least 20% lower, and more specifically at least 30% lower. In FIG. 2, currently estimated maximum NOx conversion rate of the SCR catalyst corresponding to curve B is 92%, and demanded NOx conversion rate may for example be set to 62% (point 22) during the test period.

If the catalyst degradation is not monitored, i.e. if the currently estimated maximum NOx conversion rate of the SCR catalyst always equals a new catalyst, demanded NOx conversion rate may set low enough to minimize degradation effect based on a worst case scenario, i.e. a significantly degraded SCR catalyst. This will require a significant reduction in demanded NOx conversion rate, such for example in a range of 10-50% of currently estimated maximum NOx conversion rate of said SCR catalyst, specifically in a range of 10-40%, and more specifically in a range of 10-30%.

Reduced level of demanded NOx conversion rate during the test period not only lessens the detrimental effect of a degraded SCR catalyst, but also aids in preventing ammonia slip and ammonia buffering during the test period, both of which potentially distorts the urea quality estimation. The reagent quality estimation is based on comparing the accumulated demanded NOx conversion and the actual accumulated NOx conversion during the test period, whereby the accumulated demanded NOx conversion corresponds to accumulated injected reagent level. Any ammonia slip will distort the reagent quality estimation because it is assumed that all ammonia originating from the injected reagent has been converted in the catalyst. Besides, most NOx sensors are cross-sensitive to NOx and ammonia. Ammonia slip may be registered as NOx emission during the test period, thereby distorting the registered actual SCR catalyst NOx conversion rate, and consequently also distorting the resulting urea concentration estimation. Ammonia slip out of said SCR catalyst is prevented by simply setting said demanded NOx conversion rate sufficiently low.

Furthermore, an unregistered change in the SCR catalyst ammonia buffer during the test period, for example a buffer increase, will also result in distortion of the reagent quality estimation. The urea concentration estimate of the reagent according to the invention is based on comparing the accumulated amount of injected reagent with the accumulated NOx reduction amount in the SCR catalyst during the test period, and if the ammonia buffer is changed during the test, the accumulated amount of NOx reduction in the SCR catalyst does no longer correspond to amount of ammonia originating from the accumulated amount of injected reagent, based on a predetermined model for describing the actual conversion of NOx inside the SCR catalyst. For this reason, the ammonia buffer is preferably empty, or at least substantially empty upon start of the test period, and the demanded NOx conversion rate is preferable reduced to an extent to prevent any increase in ammonia buffer during the test.

Figure 3:
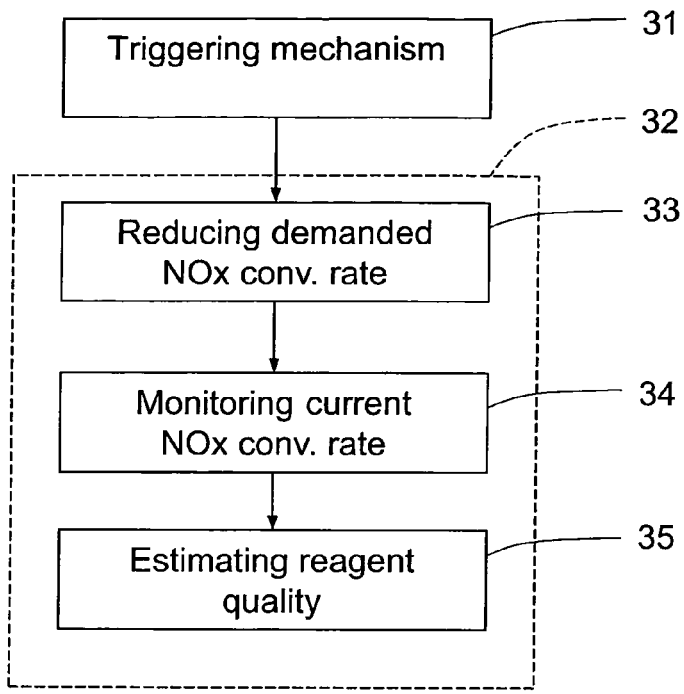
FIG. 3 shows the main steps of the method according to the invention.

FIG. 3 schematically illustrates the typical steps of the method for estimating the quality of a urea based reagent in terms of urea concentration according to the invention. Initially, a triggering mechanism 31 indicating a potential dilution of the reagent results in entering a reagent quality estimation state 32. The reagent quality estimation state 32 comprises the step 33 of setting a demanded NOx conversion rate substantially lower than a currently estimated maximum NOx conversion rate of said SCR catalyst, wherein the currently estimated maximum NOx conversion rate may be continuously monitored and adapted or fixed. The demanded NOx conversion rate may for example be set to 70% of currently estimated maximum NOx conversion rate. The buffer is here before start of the test period preferably empty, and the demanded NOx conversion rate is set low enough to prevent ammonia slip and buffer increase. Thereafter follows a step 34 including monitoring an actual NOx conversion rate for a certain time period, and thereafter a step 35 including estimating the urea concentration of said reagent based on comparing the monitored actual NOx conversion and the demanded NOx conversion during said time period.

Figure 4:
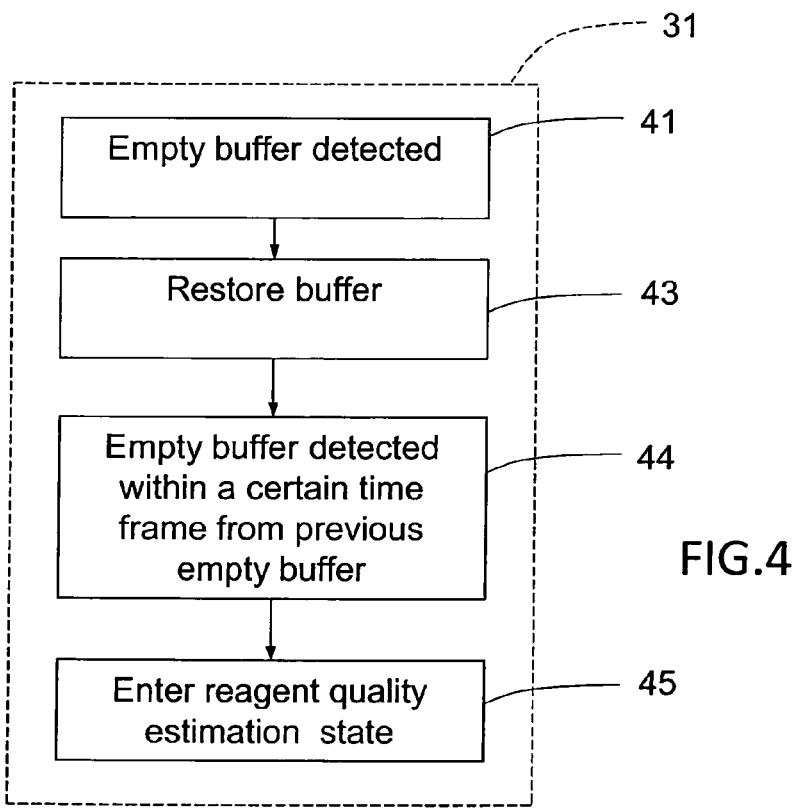
FIG. 4 shows an exemplary triggering mechanism.

The triggering mechanism 31 may have many different configurations. One triggering mechanism is disclosed in FIG. 4 having a first step 41 of detecting an empty SCR catalyst ammonia buffer. This may be detected by a sudden decrease in NOx conversion rate. In a following step 43, the ammonia buffer is restored by means of temporarily increasing the reagent injection rate. If then in a subsequent step 44 another empty buffer is detected within a certain time period from the first detected empty buffer, the control system may arrive at the assumption that the reagent is diluted, and therefore in step 45 enters the reagent quality estimation state 32.

Reference signs mentioned in the claims should not be seen as limiting the extent of the matter protected by the claims, and their sole function is to make claims easier to understand.

As will be realised, the invention is capable of modification in various obvious respects, all without departing from the scope of the appended claims.

Accordingly, the drawings and the description thereto are to be regarded as illustrative in nature, and not restrictive.

The invention claimed is:

1. Method for estimating the quality of an urea based reagent in terms of urea concentration, the reagent being injected upstream of a SCR catalyst in an exhaust aftertreatment system, comprising:
  setting a demanded NOx conversion rate substantially lower than a currently estimated maximum NOx conversion rate of the SCR catalyst, wherein a degraded and aged SCR catalyst exhibits essentially the same NOx conversion rate as a new SCR catalyst at the demanded NOx conversion rate;
  monitoring an actual NOx conversion rate for a certain time period; and
  estimating the urea concentration of the reagent based on comparing the monitored actual NOx conversion and the demanded NOx conversion during the time period.

2. The method according to claim 1, comprising additionally ensuring that any stored ammonia within the SCR catalyst does not influence the outcome of the urea concentration estimation.

3. The method according to claim 2, comprising controlling a reagent injection rate before and during the time period such that the SCR catalyst ammonia buffer remains substantially empty during the time period.

4. The method according to claim 2, comprising controlling a reagent injection rate during the time period such that an estimated SCR catalyst ammonia storage level at the start and end of the time period is the same.

5. The method according to claim 1, comprising setting the demanded NOx conversion rate such that ammonia slip out of the SCR catalyst is prevented.

6. The method according to claim 1, comprising setting the demanded NOx conversion rate at least 10% lower than currently estimated maximum NOx conversion rate of the SCR catalyst, specifically at least 20% lower, and more specifically at least 30% lower.

7. The method according to claim 1, comprising monitoring a maximum NOx conversion rate of the SCR catalyst.

8. The method according to claim 1, characterized by setting the demanded NOx conversion rate in a range of 10-50% of the currently estimated maximum NOx conversion rate of the SCR catalyst, specifically in a range of 10-40%, and more specifically in a range of 10-30%.

9. The method according to claim 1, comprising selecting the time period according to a predetermined value, or determining the time period based on actual engine and/or exhaust aftertreatment system parameters.

10. The method according to claim 1, comprising determining the time period based on accumulated level of engine NOx emission during the time period.

11. The method according to claim 1, wherein the estimation of the urea concentration of the reagent is based on calculating a ratio between the actual NOx conversion and the demanded NOx conversion, and multiplying the ratio with a factor corresponding to an expected proportion of urea in the reagent.

12. The method according to claim 1, wherein the actual NOx conversion during the time period is calculated by integrating the difference between a NOx emission level upstream of the SCR catalyst and a NOx emission level downstream of the SCR catalyst during the time period.

13. The method according to claim 1, wherein the demanded NOx conversion during the time period is calculated by integrating the product of the demanded NOx conversion rate and a NOx emission level upstream of the SCR catalyst during the time period.

14. The method according to claim 1, comprising triggering the reagent quality estimation upon determining at least two occasions within a certain time period that the SCR catalyst ammonia buffer is empty, wherein a time interval of elevated reagent dosage rate occurred between the occasions on order to restore the SCR catalyst ammonia buffer.

15. The method according to claim 1, wherein the step of setting a demanded NOx conversion rate comprises the step of controlling the amount of injected reagent upstream of the SCR catalyst in the exhaust aftertreatment system based on actual engine and/or exhaust aftertreatment system parameters.

* * * * *